(12) United States Patent
McDonald

(10) Patent No.: US 10,441,394 B2
(45) Date of Patent: Oct. 15, 2019

(54) DENTAL MATRIX BAND

(71) Applicant: Dentsply International Inc., York, PA (US)

(72) Inventor: Simon P. McDonald, Katikati (NZ)

(73) Assignee: DENTSPLY SIRONA Inc., York, PA (US)

( * ) Notice: Subject to any disclaimer, the term of this patent is extended or adjusted under 35 U.S.C. 154(b) by 354 days.

(21) Appl. No.: 14/389,556

(22) PCT Filed: Mar. 29, 2013

(86) PCT No.: PCT/US2013/034546
§ 371 (c)(1),
(2) Date: Sep. 30, 2014

(87) PCT Pub. No.: WO2013/151880
PCT Pub. Date: Oct. 10, 2013

(65) Prior Publication Data
US 2015/0182302 A1 Jul. 2, 2015

(30) Foreign Application Priority Data

| Apr. 2, 2012 | (NZ) | 599181 |
| Apr. 19, 2012 | (NZ) | 599477 |
| Oct. 12, 2012 | (NZ) | 603021 |
| Dec. 10, 2012 | (NZ) | 604244 |

(51) Int. Cl.
*A61C 5/85* (2017.01)
*A61C 13/15* (2006.01)

(52) U.S. Cl.
CPC ............ *A61C 19/003* (2013.01); *A61C 5/85* (2017.02)

(58) Field of Classification Search
CPC .......... A61C 5/125; A61C 5/85; A61C 19/003; F04C 2270/0421
See application file for complete search history.

(56) References Cited

U.S. PATENT DOCUMENTS

| 5,035,615 A | 6/1991 | Din |
| 5,330,353 A | 7/1994 | Wavrin |
| 5,380,198 A | 1/1995 | Suhonen |
| 5,807,101 A | 9/1998 | Scalzo |
| 5,975,906 A | 11/1999 | Knutson |

(Continued)

FOREIGN PATENT DOCUMENTS

| DE | 10-2006-005276 A1 | 8/2007 |
| DE | 102006005276 A1 | 8/2007 |
| EP | 0795302 A1 | 9/1997 |

OTHER PUBLICATIONS

Translated abstract of DE 10 2006 005 276.*

(Continued)

*Primary Examiner* — Heidi M Eide
(74) *Attorney, Agent, or Firm* — Dentsply Sirona Inc.

(57) ABSTRACT

The present invention relates to a dental matrix for use repairing and restoring inter-proximal cavities on a tooth with light-cured composites, the dental matrix comprising a matrix body and a plurality of light transmitting micro-pores positioned on the matrix body and overlying the inter-proximal surface of the tooth when the dental matrix engages the restored tooth. The present invention further relates to a method manufacture of such dental matrix.

9 Claims, 3 Drawing Sheets

(56) References Cited

U.S. PATENT DOCUMENTS

| | | |
|---|---|---|
| 6,350,122 B1 | 2/2002 | Meyer |
| 6,736,639 B1 | 5/2004 | Summer |
| 7,367,802 B2 | 5/2008 | Viscomi |
| 2004/0229187 A1 | 11/2004 | Bretscher |
| 2007/0154860 A1 | 7/2007 | Kerle |
| 2009/0142725 A1* | 6/2009 | Bryant .................... A61C 5/85 433/39 |

OTHER PUBLICATIONS

Translation of DE102006005276 retreived from https://patentscope.wipo.int/search/en/detail.jsf?docId=DE104724258&recNum=2&maxRec=&office=&prevFilter=&sortOption=&queryString=&tab=PCTDescription on May 2, 2017.*

International Search Report; PCT/US2013/034546; Jun. 7, 2013 (completed); dated Aug. 16, 2013.

Written Opinion of the International Searching Authority; PCT/US2013/034546; Jun. 7, 2013 (completed); dated Aug. 16, 2013.

International Preliminary Report on Patentability; PCT/US2013/034546; Jun. 2013 (completed); dated Aug. 16, 2013.

* cited by examiner

DENTAL MATRIX BAND

CROSS-REFERENCE TO RELATED APPLICATIONS

This application claims priority to International Application No. PCT/US2013/034546, filed on Mar. 29, 2013, which in turn claims priority to New Zealand Provisional Patent Application No. 599181, filed on Apr. 2, 2012, New Zealand Provisional Patent Application No. 599477, filed on Apr. 19, 2012, New Zealand Provisional Patent Application No. 603021, filed on Oct. 12, 2012, and New Zealand Non-Provisional Patent Application No. 604244, filed Dec. 10, 2012, the contents of which are all hereby incorporated by reference.

FIELD OF THE INVENTION

This invention relates to a new dental matrix device for assisting dentists to form and successfully light cure composite dental restorations on tooth surfaces, and a method for manufacturing a new dental matrix device.

SUMMARY OF THE PRIOR ART

Matrices and the use of matrix systems are well known and widely utilized in restorative dentistry. There are many types of matrices available and are generally made entirely of metal or plastic and are sectional or circumferential bands. Plastic matrices generally are thicker than metal matrices and this causes problems obtaining tight inter-proximal contacts. For this reason, metal matrices have been more popular for posterior teeth.

During the restoration of an inter-proximal cavity, the matrix band is secured around the tooth and cavity and forms a mould. This mould is filled with composite material and the composite is light cured. The difficulty with curing an inter-proximal restoration is that once the metal matrix band is wrapped around the tooth, the matrix band does not allow horizontal curing of the composite at the gingiva-proximal tooth surface. It has to be cured from above and this can lead to incomplete curing of the composite resin. When this occurs, composite resin can adhere to the metal matrix rather than the tooth and detach from the restoration when the matrix is removed. The restoration must then be re-done or repaired.

Prior art exists of metal matrices with one or two open areas covered with a membrane of transparent material and of matrices with illuminating ports with port covers. These open areas and ports cover a relatively large area of the matrix and because these openings are either covered by a port cover or covered by a very thin expanding film, in-use, they may result in restorations with poor anatomical form.

It is an object of the present invention to provide the dentist with a means of firmly retaining the composite material with a metallic matrix while enabling light curing of the composite, or to at least provide dental practitioners with a useful choice.

SUMMARY OF THE INVENTION

In a first aspect the invention consists in a dental matrix for use in repairing and restoring cavities with light-cured restorative material, the dental matrix comprising:

a metal substrate comprising a plurality of micro-apertures, wherein the micro apertures are filled with a transparent or semi transparent resin, and a polymer layer covering the metal substrate and the resin filled micro-apertures for contacting the tooth in use.

In some embodiments the transparent or semi-transparent resin used to fill the micro-apertures is also used to form the polymer layer covering the metal substrate.

In some embodiments the polymer layer is formed of a polymer that does not stick to the dental restorative material, the polymer layer forming a smooth non-stick surface finish.

In some embodiments the polymer layer is a fluorocarbon. In some embodiments the fluorocarbon is polytetra-fluoro-ethylene. In some embodiments the fluorocarbon is fluorinated ethylene propylene. In some embodiments the fluorocarbon is perfluoroalkoxy.

In some embodiments the polymer layer has a thickness of 25 micron or less.

In some embodiments the dental matrix comprises a layer of the resin on a side of the dental matrix opposite the polymer layer. In some embodiments the dental matrix has no layer of resin on a side of the dental matrix opposite the polymer layer.

In some embodiments the metal substrate is a foil.

In some embodiments the metal substrate is a stainless steel substrate.

In some embodiments the metal substrate has a thickness of 20-50 micron.

In some embodiments each of the plurality of micro-apertures has an area of between 300 and 80,000 square microns.

In some embodiments the plurality of micro-apertures comprises circular micro-apertures.

In some embodiments the plurality of micro-apertures comprises hexagonal micro-apertures. In some embodiments the plurality of micro-apertures comprises oval micro-apertures. In some embodiments the plurality of micro-apertures comprises elongate micro-apertures or slots each having a length greater than a width. In some embodiments a width of each of the elongate micro-apertures or slots is 50 to 180 micron. In some embodiments each elongate aperture has a length and a width and a ratio of the length and the width is 1.2 to 5. In some embodiments the ratio of the width of each of the plurality of micro-apertures and the thickness of the metal substrate is greater than 2. In some embodiments the ratio of the width of each of the plurality of micro-apertures and the thickness of the metal substrate is greater than 3. In some embodiments each of the plurality of micro-apertures is circular and 20 to 180 micron in diameter. In some embodiments the ratio of the diameter of each of the plurality of micro-apertures and the thickness of the metal substrate is greater than 2. In some embodiments the ratio of the diameter of each of the plurality of micro-apertures and the thickness of the metal substrate is greater than 3.

In some embodiments the micro-apertures are arranged in a concentric partial archway pattern. In some embodiments the micro-apertures are arranged in a honeycomb pattern. In some embodiments the plurality of micro-apertures comprises elongate micro-apertures each having a length greater than a width, and at least some of the elongate micro-apertures being arranged in concentric partial rings 4 about a centre or centre region each with its length aligned approximately towards the centre or centre region. In some the centre or centre region may be located on the dental matrix to be positioned between the lingual side of the tooth and the buccal side of the tooth in use. In some the centre or centre region is positioned on the dental matrix, in use the elongate micro-apertures located above the centre each with its length aligned approximately towards the centre or centre region and the elongate micro-apertures located below the centre each with its length aligned approximately horizontally. In some embodiments the elongate micro-apertures located below the centre are arranged in columns. In some embodiments the centre is located adjacent a bottom edge of the dental matrix. In some embodiments the plurality of micro-apertures comprises two groups of micro-apertures, each group of micro-apertures comprising elongate micro-apertures each having a length greater than a width, and at least some of the elongate micro apertures being arranged in concentric partial rings 4 about a centre or centre region each with its length aligned approximately towards the centre or centre region. In some embodiments the two groups of micro-apertures are located either side of a centre line of the dental matrix.

In some embodiments the thickness of the dental matrix is less than 60 micron. In some embodiments the thickness of the dental matrix is less than 50 micron. In some embodiments the thickness of the dental matrix is less than 45 micron.

In some embodiments the dental matrix is a sectional matrix. In some embodiments the dental matrix is a shaped circumferential band. In some embodiments the dental matrix is a straight edged circumferential band.

In a second aspect the invention consists in a dental matrix for use in repairing and restoring cavities with light-cured restorative material, the dental matrix comprising:
  a metal substrate comprising a plurality of micro-apertures, wherein the plurality of micro-apertures comprises elongate micro-apertures each having a length greater than a width, and at least some of the elongate micro apertures being arranged in concentric partial rings 4 about a centre or centre region each with its length aligned approximately towards the centre or centre region.

In some embodiments the centre or centre region may be located on the dental matrix to be positioned between the lingual side of the tooth and the buccal side of the tooth in use.

In some embodiments the centre or centre region is positioned on the dental matrix, in use the elongate micro-apertures located above the centre each with its length aligned approximately towards the centre or centre region and the elongate micro-apertures located below the centre each with its length aligned approximately horizontally.

In some embodiments the elongate micro apertures located below the centre are arranged in columns.

In some embodiments the centre is located adjacent a bottom edge of the dental matrix.

In some embodiments the plurality of micro-apertures comprises two groups of micro-apertures, each group of micro-apertures comprising elongate micro-apertures each having a length greater than a width, and at least some of the elongate micro apertures being arranged in concentric partial rings 4 about a centre or centre region each with its length aligned approximately towards the centre or centre region.

In some embodiments the two groups of micro-apertures are located either side of a centre line of the dental matrix.

In some embodiments the micro-apertures are arranged in a concentric archway pattern.

In a third aspect the invention consists in a method of forming a dental matrix for use in repairing and restoring cavities in a tooth with light-cured composites, the method comprising:
  i) providing a metal substrate,
  ii) coating a side of the metal substrate with a polymer to form a polymer layer on a side of the dental matrix for contacting the tooth in use,
  iii) forming micro-apertures in the metal substrate by photo etching a reverse side of the metal substrate without breaking the polymer layer.

In some embodiments the method comprises:
  iv) filling the micro-apertures with a transparent or semi-transparent resin.

In some embodiments the method comprises applying the resin to the metal substrate by an apparatus that simultaneously fills the micro apertures and removes substantially all resin from the reverse side of the dental matrix. In some embodiments the method comprises applying the resin to the metal substrate by an apparatus that simultaneously fills the micro apertures and leaves a layer of resin on the reverse side of the dental matrix.

In some embodiments the apparatus comprises one or more of a roller and a squeegee or blade like apparatus.

In some embodiments the method comprises providing a parent metal substrate and subsequently separating the dental matrix from the parent metal substrate.

In some embodiments the method comprises photo etching at least a portion of a perimeter of the dental matrix for separating the dental matrix from the parent metal substrate, and separating the dental matrix from the parent metal substrate by breaking the polymer coating at the perimeter of the dental matrix.

In some embodiments the method comprises adding a photo-resistive film to the reverse side of the metal substrate after the coating is added to the metal substrate.

In some embodiments the method comprises providing the parent metal substrate as a metal strip.

In some embodiments the metal strip is provided in a coil, and the method comprises unwinding the metal strip from the coil for the polymer layer to be applied.

In some embodiments the method comprises spraying the polymer onto a surface of the metal substrate, and heating the metal substrate with sprayed polymer in an oven to form the polymer layer on the metal strip.

In some embodiments the method comprises applying the resin to the metal substrate using a squeegee or blade like apparatus for spreading the resin into the apertures.

In some embodiments the method comprises applying the resin to the metal substrate using a squeegee or blade like apparatus for spreading the resin into the apertures and to leave a layer of resin on the reverse side of the dental matrix.

In some embodiments the method comprises applying the resin to the metal substrate using a squeegee or blade like apparatus for spreading the resin into the apertures and to substantially remove all resin from the reverse side of the dental matrix.

In some embodiments the polymer is a fluorocarbon to form a fluorocarbon layer. In some embodiments the polymer is polytetra-fluoroethylene to form a polytetrafluoroethylene layer.

In some embodiments the polymer layer has a thickness of 25 micron or less. In some embodiments the method comprises the resin is one of a fluorocarbon, polytetrafluoroethylene, a polyester.

In some embodiments the method comprises the metal substrate is a foil.

In some embodiments the method comprises the metal substrate is a stainless steel substrate.

In some embodiments the method comprises the metal substrate has a thickness of 20-50 micron.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

The invention consists in the foregoing and also envisages constructions of which the following gives examples only.

BRIEF DESCRIPTION OF THE DRAWINGS

A preferred embodiment of the present invention will now be described with reference to the accompanying drawings in which.

DETAILED DESCRIPTION OF THE PRESENT INVENTION

Figure 1:
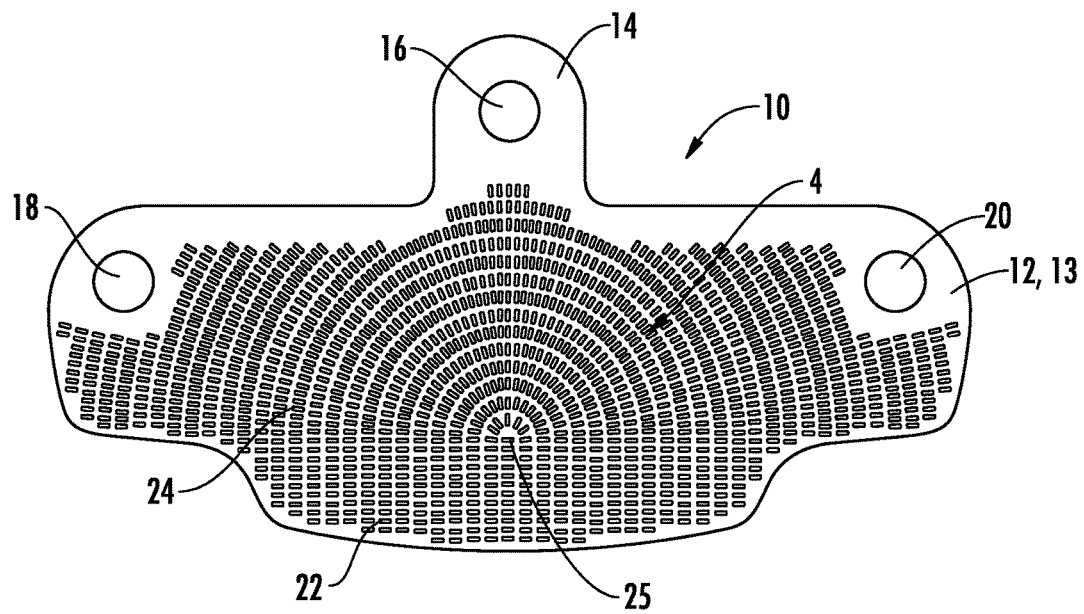
FIG. 1 illustrates a dental matrix according to one embodiment of the present invention.
Figure 2:
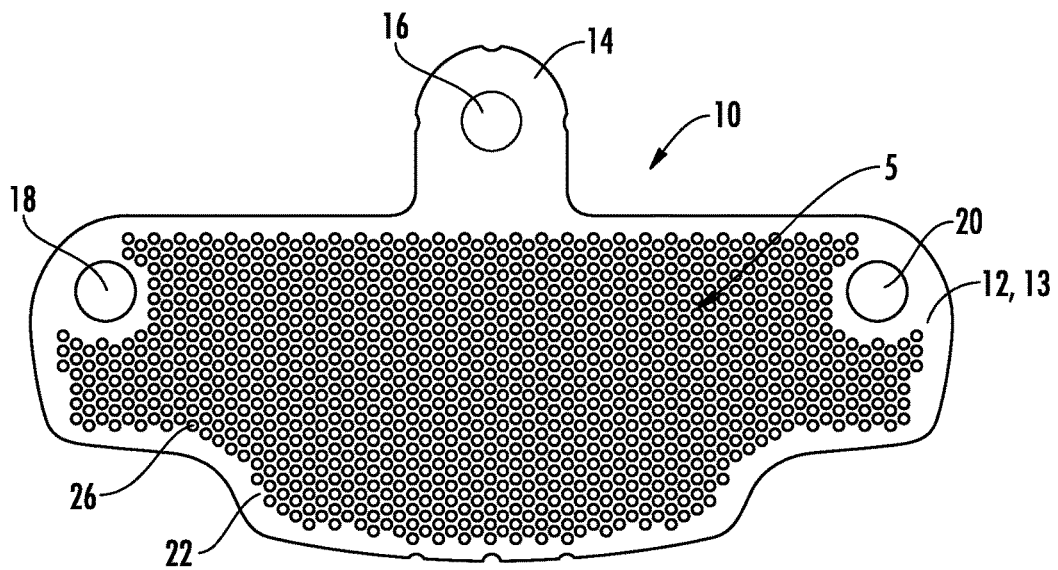
FIG. 2 illustrates a dental matrix according to another embodiment of the present invention.
Figure 3:
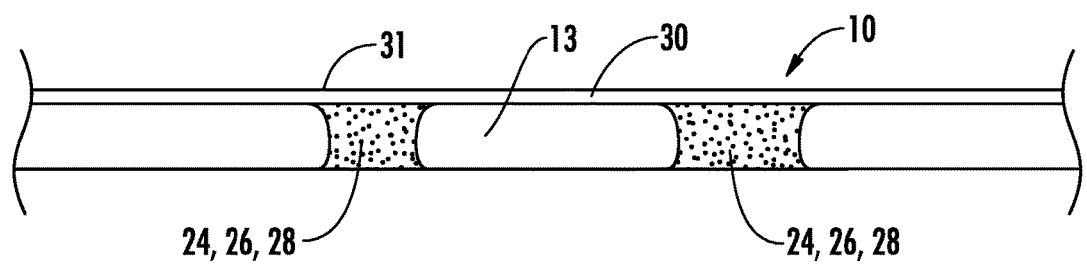
FIG. 3 illustrates a schematic part cross section of a dental matrix according to one embodiment of the present invention.

A dental matrix band comprising features of the present invention is described with reference to FIGS. 1 to 3. FIG. 1 shows a first embodiment of the present invention consisting of a sectional matrix, and FIG. 2 shows an alternative embodiment. FIG. 3 shows a cross section through a dental matrix comprising features of the present invention. Whenever possible, common reference numbers will be utilized to refer to common elements and features in each of the embodiments described.

Each dental matrix 10 illustrated in FIGS. 1 and 2 comprises a matrix body 12 having a tab 14 with a first bore 16 disposed on the top border of the matrix body 12 and a second and third bore 18, 20 disposed adjacent to either side edge of the matrix body 12. Tab 14 provides the dentist with a section of material where the matrix can be grabbed with a dental instrument and moved into or out of position in the patient's mouth. The first, second and third bores 16, 18, 20 further assist in the dentist in placing, positioning, and extracting the matrix 10 and are particularly useful when the dentist is using a pinned tweezers or other dental instrument having a pin or hook for attaching to various items. The matrix body 12 terminates at its lower margin at a flange portion 22 at the lower portion of the matrix body 12. The flange portion 22 addresses the tooth being restored at the gingival margin. While the dental matrices 10 shown each includes a gingival flange portion 22, tab 14 and holes 16, 18 and 20, it is contemplated that the dental matrix can be manufactured with only a dental matrix body 12 and without a gingival flange portion or tab 12 or holes 16, 18 and 20 without falling outside the scope of the invention. When the dental matrix 10 is without a gingival flange portion, the bottom edge of the dental matrix body 12 forms the bottom edge of the dental matrix 10.

In one embodiment, the matrix body 12 exhibits a degree of curvature along both its longitudinal axis (horizontal axis in use) and latitudinal axis (vertical axis in use), thus enabling the matrix body 12 to be formed into a shape complementary with and against a tooth be restored.

The matrix body 12 is formed from a metal substrate or foil 13, for example a stainless steel foil. Preferably the metal substrate has a thickness of 20 to 50 micron (micrometer, µm).

As shown in FIGS. 1 and 2, the matrix body 12 further comprises a plurality of light-transmitting micro-apertures 24, 26. Preferably the micro-apertures generally cover a majority of the matrix body 12 and flange portion 22, and at least an area of the matrix body that in use overlays the inter-proximal surface of a tooth to be restored.

The micro-apertures 24, 26 are positioned on the matrix body 12 and gingival flange portion 22 such that when the matrix 10 is formed into the desired configuration around the tooth being restored, the micro-apertures 24, 26 align with the interproximal tooth surface of the tooth being restored.

In the embodiment shown in FIG. 2, each micro-aperture is substantially circular and is approximately 20 to 180 micron in diameter. In one embodiment a ratio of the diameter of the micro-apertures and the thickness of the metal substrate of the matrix is greater than 2. In another embodiment a ratio of the diameter of the micro-apertures and the thickness of the metal substrate of the matrix is greater than 3. When light is shined through the matrix, the thickness of the matrix and the aperture size determines the amount of light that can pass through the matrix for a given angle 15 of incidence of light to the plane of the matrix. For example, for a ratio of greater than 2, the angle of incidence for light to pass through the matrix must be greater than about 27 degrees. For a ratio of greater than 3, the angle of incidence for light to pass through the matrix must be greater than about 19 degrees.

The micro-apertures can be different shapes and configurations, including elongated apertures such as slots as shown in the embodiment of FIG. 1, hexagonal shaped apertures or oval apertures (not illustrated) for example.

Referring to the embodiment of FIG. 1, the micro-apertures 24 consist of elongated apertures or slots having a length of approximately 50 to 180 micron. Preferably the length is 1.2 to 5 times the width of the slots. In one embodiment a ratio of the width of the micro-apertures and the thickness of the metal substrate of the matrix is greater than 2. In another embodiment a ratio of the width of the micro-apertures and the thickness of the metal substrate of the matrix is greater than 3.

The micro-apertures 24, 26 can be arranged in a number of different configurations. In FIG. 2, the substantially circular micro-apertures are arranged in a staggered or honey comb configuration 5. In an alternative embodiment the micro-apertures may be aligned in columns.

In the embodiment of FIG. 1, at least some of the slots 24 are arranged in concentric rings 4 about a centre or centre region 25, each slot with its length aligned approximately towards the centre. The arrangement of apertures 24 in the embodiment of FIG. 1 may be described as a concentric archway pattern. As illustrated, the centre may be located centrally between side edges of the dental matrix, or located between the lingual side of the tooth and the buccal side of the tooth to be treated in use.

As shown in FIG. 1, the centre 25 may be positioned on the dental matrix (within the perimeter of the dental matrix). In the illustrated embodiment, the slots located above the centre 25 are each arranged with its length aligned approximately towards 10 the centre 25. The slots located below the centre each have its length aligned approximately horizontally. As shown, the slots arranged horizontally are formed in columns, however these slots may be arranged in a staggered arrangement, like the circular apertures in the embodiment of FIG. 2. Further, the apertures below the centre, for example on the area of the flange portion 22, may be other shapes, for example circular. In a further alternative embodiment that does not comprise a flange portion 22, the centre 25 of the aperture pattern may be located at or near to a bottom edge of the matrix. In a further alternative embodiment, non-elongated micro apertures may be arranged in a concentric archway pattern. For example, circular apertures may be formed in a concentric partial archway pattern with the circular apertures arranged in concentric partial rings 4 about a centre or centre region.

The alignment of the slots or elongate apertures (for example oval or other elongated shape) in the embodiment illustrated in FIG. 1 facilitates light entry of light beams from a curing light source into the micro-apertures at an angle from above normal to the plane of the matrix. The micro-apertures also allow light to enter from substantially horizontal to the plane of the matrix. Arranging elongated micro-apertures in the circular manner with respect to a centre 25 reduces or eliminates the need to align the light source directly perpendicular or normal to the matrix, which becomes increasingly difficult as the micro-apertures fall further into the inter-proximal space, while still enabling maximum light transmission through the dental matrix.

It is desired that that the interior surface of the matrix 10 be smooth and free from blemishes or imperfections that may transferred to the composite material and formed into the restoration. To maintain the smooth interior surface of the matrix 10 that contacts the tooth in use, the individual micro-apertures are filled with a transparent, light transmitting material 28, as illustrated in the cross sectional view of FIG. 3. Preferably, the micro-apertures are filled with a resin or polymer, for example one of a fluorocarbon or a polyester. It is contemplated that any suitable transparent or semitransparent, light transmitting material may be used to fill the micro-apertures. A suitable resin may have a compressive strength of about 7,000 psi (ASTM D695). A suitable resin may have a flexural modulus of about 50,000-65,000 psi (ASTM D790). A suitable resin may have a tensile strength of about 3,000 psi to 6,000 psi (ASTM D638). A suitable resin may have an elongation of about 25% (ASTM D2370). The resin may comprise a urethane resin. The resin may comprise compounds to enhance release properties. For example the resin may comprise one or more of co-polymerisable silicone and polyethylene wax. The resin may comprise components to enhance adhesion to the substrate. For example the resin may comprise an acid coupling agent.

Figure 4:
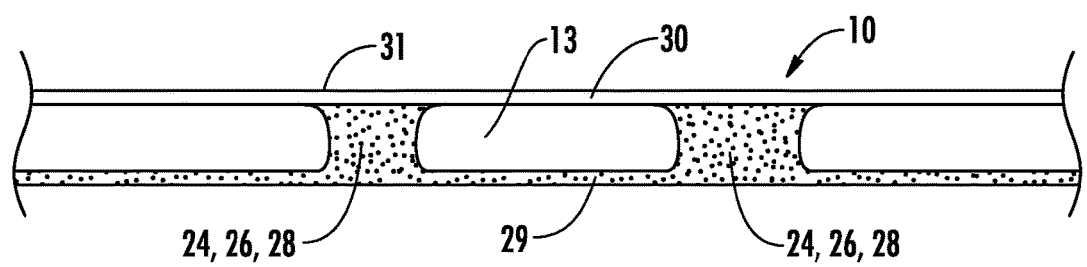
FIG. 4 illustrates a schematic part cross section of a dental matrix according to another embodiment of the present invention.

In one embodiment illustrated in FIG. 4, the apertures 24 are filled with resin and a resin layer 29 is also formed or provided to the exterior surface of the matrix that does not contact the tooth to be treated in use. In the embodiment illustrated in FIG. 3, there is no resin layer or a very thin resin layer on the exterior surface of the matrix. This form of the matrix provides a thinner matrix which is preferred.

Preferably the thickness of the matrix illustrated in either FIG. 3 or 4 is less than 60 micron. More preferably the thickness is less than 50 micron, and most preferably the thickness is less than 45 micron, for example a thickness of around 40 micron.

Also, as illustrated in FIG. 3, a transparent, light transmitting film 30 is provided to the surface of the dental matrix 10 that contacts the tooth in use. The film or layer 30 covers the metal substrate 13 and the resin filled micro apertures and presents a smooth surface 31 for contact with the tooth. Preferably, the film 30 is a polymer layer, for example a fluorocarbon layer such as polytetra-fluorocarbon, for example 5 Dupont's Teflon®, Whitford Corporation's Xylan® or other suitable alternative material such as fluorinated ethylene propylene, or perfluoroalkoxy. Preferably the polymer layer is formed of a polymer that does not stick to the dental restorative material so that the polymer forms a non-stick smooth surface finish. In one embodiment, the polymer layer 30 is formed from the resin used to fill the micro-apertures. Preferably the thickness of the polymer layer is 25 micron or less.

Figure 5:
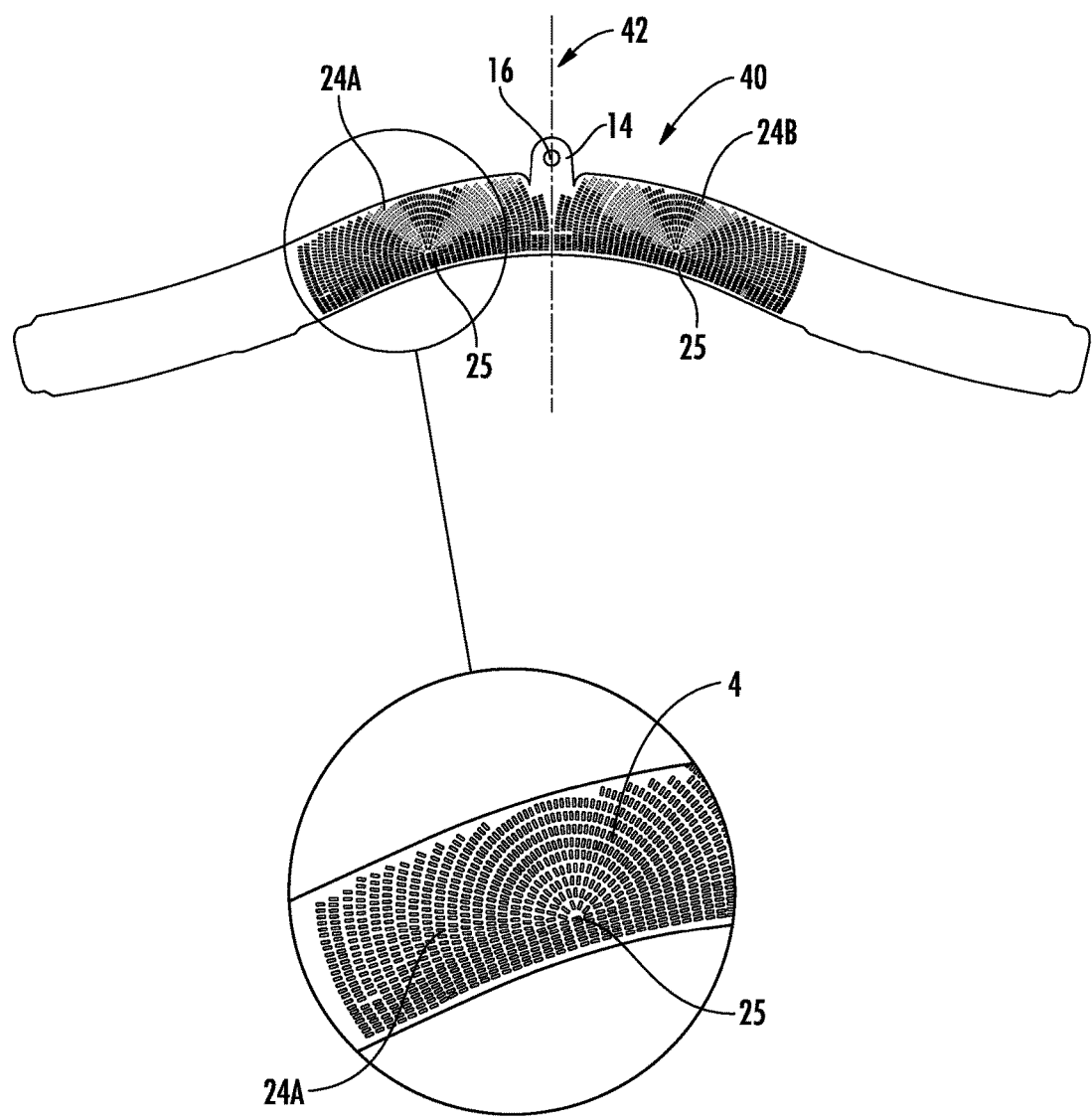
FIG. 5 illustrates a shaped circumferential band dental matrix according to another embodiment of the present invention.

An alternative matrix is illustrated in FIG. 5. The matrix of FIG. 5 is a shaped circumferential band. The matrix of FIG. 5 comprises a grouping of micro-apertures positioned to one side of a centre line 42 of the matrix. In the illustrated embodiment, the matrix comprises two groupings of micro-apertures 24A and 24B. Each grouping of micro apertures comprises a concentric archway pattern as described with reference to the embodiment of FIG. 1. Each grouping 24A and 24B comprises slots arranged in concentric rings 4 about a centre or centre region 25, each slot with its length aligned approximately towards the centre. In use, the centre 25 of each grouping of apertures may be located between the lingual side of the tooth and the buccal side of the tooth to be treated, or on the lingual side of the tooth or the buccal side of the tooth to be treated.

Other variations described with reference to the embodiment of FIG. 1 may be incorporated into a circumferential matrix band as described with reference to the embodiment of FIG. 5.

The new dental matrix 10 operates in the following manner. First, the dentist prepares an inter-proximal cavity on the surface of the tooth being restored to receive the light-cured composite/restoration material. The dental matrix 10 is then inserted into the interproximal space and held securely against the tooth being restored with a retaining device. Next, to ensure there is no leaking of the composite between the dental matrix 10 and tooth, a dental wedge may be inserted into the inter-proximal space to hold the dental matrix 10 firmly against the surface of the tooth being restored. The wedge may be inserted before or after a retaining device is applied to hold the matrix in place. Once the dental matrix 10 is secured in position, the cavity is then filled with composite material. Finally, the composite is light-cured from an occlusal direction as per normal but can also be cured horizontally through the micro-apertures in the dental matrix.

Method of Manufacture

A method for manufacturing a dental matrix band comprising features of the present invention is described below.

A metal substrate is coated on one side with a film or layer 30. Preferably the metal substrate has a thickness of 20 to 50 micron, To apply the layer 30 on the substrate, the coating material 30 may be sprayed on to a surface of the metal substrate. For example, a fluorocarbon such as polytetra-fluorocarbon, for example Dupont's Teflon® is sprayed onto a surface of the metal substrate. The applied coating and metal substrate is preferably baked in an oven to dry or set the coating material on the substrate to form the film or layer

30. For example the substrate and applied coating material is baked in an oven at a temperature of about 360° C. to about 400° C. In some embodiments, the substrate with coating is baked or cured in an oven for about 30 seconds or less than 30 seconds. In some embodiments, the metal substrate is preheated before the coating material is applied. For example, the metal substrate is preheated in an oven at a temperature of about 400° C. to about 420° C. In some embodiment, the metal substrate is preheated for period of about 10 seconds, or less than 10 seconds. In some embodiments, the substrate with coating is subjected to a pre-drying process by heating with infrared radiation prior to baking in an oven. In some embodiments, the coating is heated by infrared radiation at about 100° C., or about 90° C. to 100° C. In some embodiments, the substrate with coating is preheated by infrared radiation for a period of about 20 seconds, or less than 20 seconds. Preferably the coating has a thickness of less than about 25 microns.

After the coating has been applied to the metal substrate, micro-apertures 24, 26 are formed in the metal substrate by photo etching the metal substrate from a reverse or opposite side of the metal substrate.

A reverse or opposite side to the coated side of the metal substrate comprises a photo-resisting film. The photo resistive film or layer may be applied before or after the coating 30 is applied to the metal substrate. For example, a side of the metal substrate is cleaned with a cleaning solution, for example a caustic degreaser. The cleaned surface is then coated with a UV light sensitive photo resist. A stencil and/or imaging system may be used to expose a desired configuration for the micro-apertures on the photo resistive film. Other features of the matrix may also be exposed on the photo resist. Exposure, for example using UV light, prepares areas of the resisting film to form a resistant film on the surface of the substrate. The substrate is then washed, for example with a developing solution, to wash away unexposed photo-resisting film to expose the metal substrate according to a pattern produced by the stencil or imaging system. Areas of the exposed photo resist remain on the surface of the metal substrate. The photo-resist film and developing solution may be any suitable commercially available films and solutions suitable for use in the photo etching process. The metal substrate with developed film is 10 then etched to dissolve the metal exposed through the photo restive film. For example the metal substrate with developed resistive film and coating 30 is placed in a etching bath and the exposed metal of the substrate is removed by chemical etching. The etchant may be an aqueous solution of acid, for example ferric chloride. In one embodiment the etchant is heated and directed under pressure at the substrate coated with developed photo resist film. The etchant reacts with the unprotected surfaces of the metal substrate to corrode the metal quickly. After etching, the metal substrate with coating 30 is washed and rinsed to neutralize and/or remove the etchant. The etched metal substrate may be cleaned and dried. Photo resist film remaining on the surface of the metal substrate may be removed, for example by chemically removing the photo resist layer with a suitable resist stripper, and the metal substrate comprising micro-apertures may be cleaned and dried.

In some embodiments the polymer coating is not affected by the chemicals used in the etching process. Therefore the photo etching process for forming the micro-apertures does not damage the coating on the surface of the metal substrate 30. Therefore the manufacturing process described produces a matrix band comprising metal substrate with micro-apertures, and a polymer layer covering a side of the metal substrate and the micro apertures in the metal substrate. The micro-apertures are etched away leaving only a layer of polymer over each micro-aperture.

Preferably a parent metal substrate is prepared with a plurality of matrix bands for subsequent division from the parent metal substrate into individual matrix bands comprising the metal substrate with micro apertures and polymer coating. For example, in some embodiments, a continuous strip of metal substrate is coated with polymer. In some embodiments, a continuous strip metal substrate is passed through a continuous coating line. In some embodiments a continuous coating line comprises one or more of preheating the metal strip, spray coating the strip with a polymer coating, infrared pre-drying and oven curing. The polymer coated strip is then passed through the photo etching process to prepare many dental matrices along the strip. Following the etching process the strip may be passed through a press-tool and/or cutting dies to stamp each matrix from the strip. For example, a press tool is may be configured to accept a continuous strip being fed into the tool by a tractor-feed mechanism. In some embodiments, in a stamping process 3-dimensional forms can be pressed into the metal substrate.

In some embodiments, an outline or perimeter of the matrix band is etched in the photo etching process. The perimeter of the matrix may be incorporated into the stencil and/or imaging system to be etching together with the etching of the micro-apertures. For example, substantially the full perimeter of the matrix band can be etched, or the full perimeter of the matrix band may be etched. Where the full perimeter of the matrix band is etched, each individual matrix band may be retained in position in the parent metal substrate by the polymer coating. Each individual matrix may be separated from the parent substrate by breaking or cutting the polymer coating at the perimeter of the matrix. For example, the matrix may be pressed out with a forming tool for forming the matrix into a 3-dimensional configuration. In some embodiments, the matrix is shaped by a first conventional press tool, and pushed out of the parent material by a second forming tool. The perimeter of the matrix may be shaped to include tabs 14. Other features, for example holes 16, 18 and 20 may be etched in the photo etching process. By etching away the outline periphery of the matrix, the matrix is separated from the parent metal substrate without the requirement for cutting dies or the like. Press tooling and cutting dies require frequent repair and maintenance. Their elimination can result in an improvement in manufacturing efficiency, and/or savings in manufacturing costs.

The manufacturing method enables the production of micro apertures in the matrix that are covered on one side by a polymer layer. The micro-apertures allow light to pass through making the metal matrix 'transparent'.

In some embodiments the method comprises filling the micro apertures with resin 28. In some embodiments the resin is applied to the metal substrate by an apparatus that simultaneously fills the micro apertures and removes substantially all resin from the reverse side of the dental matrix. In some embodiments the resin is applied to the metal substrate by an apparatus that simultaneously fills the micro apertures and leaves a thin layer 30 of resin on the reverse side of the dental matrix. In some embodiments the resin may be spread over the surface and forced into the micro apertures by a roller or rollers. The metal substrate comprising micro-apertures and polymer coating and with resin applied to the reverse side of the metal substrate may be passed through rollers for forcing the resin into the micro apertures. In some embodiments the resin may be provided to a roller and the roller being in contact with the reverse side of the matrix presses the resin into the apertures. In some embodiments the roller may leave a thin layer 30 of resin on the reverse side of the dental matrix. In some embodiments, the roller may remove substantially all resin from the reverse side of the dental matrix to achieve the cross section illustrated in FIG. 3. In some embodiments the resin may be applied to the metal substrate using a squeegee or blade like apparatus for spreading the resin into the apertures. In some embodiments, the squeegee may leave a thin layer 30 of resin on the reverse side of the dental matrix. In some embodiments, the squeegee may remove substantially all resin from the reverse side of the dental matrix to achieve the cross section illustrated in FIG. 3. In some embodiments a squeegee or blade like instrument is used to remove recess resin from the reverse side of the dental matrix after the resin has been provided to the micro-apertures, for example by a roller or rollers. Preferably the micro-apertures are filled with resin prior to separating the dental matrix from the parent metal substrate. In the embodiment illustrated in FIG. 4, the layer of resin 4 is broken or cut at the perimeter of the dental matrix to separate the dental matrix 10 from the parent substrate.

The foregoing description of the invention includes preferred forms thereof. Modifications may be made thereto without departing from the scope of the invention as defined by the accompanying claims.

The invention claimed is:

1. A dental matrix for use in repairing and restoring inter-proximal cavities with light-cured restorative material, the dental matrix comprising:
    a first side and a second side,
    a metal substrate on the first side comprising a plurality of hexagonal micro-apertures arranged in a honeycomb pattern, wherein the hexagonal micro-apertures are filled with a transparent or semi transparent resin, and
    a polymer layer on the second side covering both the metal substrate and the resin filled hexagonal micro-apertures for contacting the tooth in use,
    wherein the transparent or semi transparent resin and the polymer layer are made of different materials;
    wherein the polymer layer on the second side includes a fluorocarbon that does not stick to a dental restorative material, the polymer layer forming a smooth non-stick surface finish;
    wherein each of the plurality of hexagonal micro-apertures has an area of between 300 and 80,000 square microns; and
    the plurality of hexagonal micro-apertures are positioned on the metal substrate such that when the dental matrix is formed into desired configuration around the tooth being restored, the plurality of hexagonal micro-apertures align with inter-proximal tooth surfaces of the tooth being restored.

2. The dental matrix of claim 1, wherein the fluorocarbon is selected from the group consisting of polytetrafluoroethylene, fluorinated ethylene propylene, and perfluoroalkoxy.

3. A dental matrix for use in repairing and restoring cavities with light-cured restorative material, the dental matrix comprising:
    a metal substrate comprising an arrangement of a plurality of micro-apertures, wherein the plurality of micro-apertures comprises elongate micro-apertures each having a length greater than a width, a first set of an at least some of the elongate micro-apertures being arranged in concentric partial rings about a centre region with each length of the at least some of the elongate micro-apertures aligned and oriented approximately radially towards the centre region, thereby eliminating the need to align a light source directly perpendicularly or normal to the dental matrix, and a second set of the elongate micro-apertures located at or near to a bottom edge of the dental matrix with their lengths aligned approximately horizontally,
    wherein the centre region being centre of the arrangement of the micro-apertures arranged in the concentric partial ring.

4. The dental matrix of claim 3, the centre region being located near the middle of the dental matrix such that the dental matrix can be positioned between a lingual side of a tooth in use and a buccal side of the tooth in use to direct light onto the light-cured restorative material.

5. The dental matrix of claim 3, wherein the second set of the elongate micro apertures located at or near to the bottom edge of the dental matrix are arranged in columns.

6. The dental matrix of claim 3, wherein the first set and the second set of micro-apertures are located on either side of a centre line of the dental matrix wherein the centre line is perpendicular to a bottom edge of the dental matrix and passes through the centre region.

7. The dental matrix of claim 3 wherein the metal substrate further comprises the plurality of elongate micro-apertures filled with a transparent or semi transparent resin, and the dental matrix further comprises a polymer layer covering the metal substrate and the resin filled micro-apertures for contacting the tooth in use.

8. The dental matrix of claim 3 wherein a ratio of the length to the width is from 1.2 to 5.

9. The dental matrix of claim 3 wherein a ratio of the width of each of the plurality of micro-apertures to a thickness of the metal substrate is greater than 2.

* * * * *